United States Patent [19]

Schönafinger et al.

[11] Patent Number: 5,399,569
[45] Date of Patent: Mar. 21, 1995

[54] SALTS OF 3-(CIS-2,6-DIMETHYLPIPERIDINO) SYDNONE IMINE

[75] Inventors: Karl Schönafinger, Alzenau; Eckard Kujath, Maintal; Dieter Voegele, Bruchköbel, all of Germany

[73] Assignee: Cassella AG, Frankfurt am Main, Germany

[21] Appl. No.: 58,770

[22] Filed: May 10, 1993

[30] Foreign Application Priority Data

May 16, 1992 [DE] Germany .................. 42 16 310.2

[51] Int. Cl.$^6$ ................. A61K 31/435; C07D 413/04
[52] U.S. Cl. ................... 514/326; 514/318; 546/209; 548/125
[58] Field of Search ............ 546/209; 548/125; 514/318, 326

[56] References Cited

U.S. PATENT DOCUMENTS

| | | | |
|---|---|---|---|
| 4,845,091 | 7/1989 | Schonafinger | 514/212 |
| 4,937,241 | 6/1990 | Schonafinger et al. | 514/227.5 |
| 5,120,732 | 6/1992 | Schonafinger | 514/236.2 |
| 5,221,680 | 6/1993 | Schonafinger | 514/326 |

FOREIGN PATENT DOCUMENTS 327808 8/1989 European Pat. Off. .

OTHER PUBLICATIONS

"Journal of Cardiovascular Pharm.", vol. 18, No. 4, Raven Press, NY, 1991, pp. 522–527.
"Circulatory Shock", vol. 38, No. 3, 1992 Publication pp. 209–216.

*Primary Examiner*—Celia Chang
*Attorney, Agent, or Firm*—Perman & Green

[57] ABSTRACT

The present invention relates to 3-(cis-2,6-dimethylpiperidino)sydnone imine salts of the general formula I

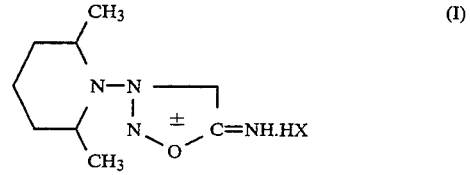

in which X denotes H$_2$PO$_4$ or

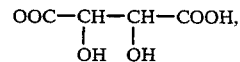

processes for their preparation and their use.

4 Claims, No Drawings

SALTS OF 3-(CIS-2,6-DIMETHYLPIPERIDINO) SYDNONE IMINE

BACKGROUND OF THE INVENTION

1. Field of the Invention

The present invention relates to 3-(cis-2,6-dimethylpiperidino)sydnone iminium dihydrogen phosphate and hydrogen tartrate, processes for their preparation and their use.

2. Discussion of the Prior Art 3-(2,6-Dimethylpiperidino)sydnone imine hydrochloride and its pharmacological properties have already been described in EP-B 327,808. However, it has the disadvantage that, on standing, it absorbs water under the influence of atmospheric humidity. The amount of absorbed water here is dependent on the temperature and the relative atmospheric humidity.

The hydrochloride is thus barely utilisable for the standardisation of pharmaceutical preparations, for which precisely defined amounts of active compound are prescribed by the legislature. The stability of pharmaceutical preparation forms, such as, for example, tablets, is also not conferred.

The object of the present invention is to bring the active compound into a non-hygroscopic form which fulfils the pharmaceutical requirements.

SUMMARY OF THE INVENTION

This object is achieved in a surprising manner by a 3-(cis-2,6-dimethylpiperidino)sydnone imine salt of the general formula I

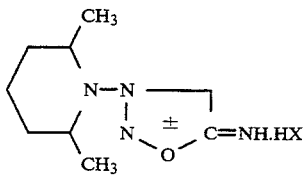 (I)

in which
X denotes $H_2PO_2$ or

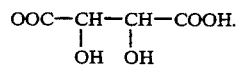

The compounds of the general formula I are not hygroscopic and therefore have previously unforeseen advantages in the production of suitable pharmaceutical forms. In the case of the production of solutions, as are required for i.v. administration, they additionally have the advantage that they set a weakly acidic pH in aqueous medium, which is favourable for the stability of the sydnone imine and acceptable for parenteral administration.

The compounds of the general formula I can be prepared, for example, by treating a compound of the general formula II

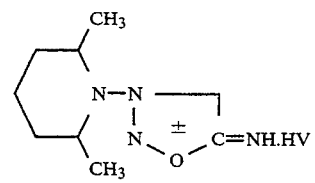 (II)

in which HV represents any desired acid, such as, for example, hydrochloric or sulphuric acid, in a solvent with tartaric acid or phosphoric acid and an inorganic or organic base.

Suitable solvents are, for example, water, alcohols such as methanol, ethanol, butanol or i-propanol, water-alcohol mixtures, acetonitrile, acetone, DMSO, DMF and mixtures thereof with water.

Suitable inorganic or organic bases are, for example, sodium hydrogen carbonate, sodium carbonate, potassium hydrogen carbonate, potassium carbonate, sodium acetate, lithium hydroxide, sodium hydroxide solution or potassium hydroxide solution, ammonia, triethylamine or pyridine.

The sequence of the addition of tartaric or phosphoric acid and base is completely non-critical and can be altered as desired.

The anion exchange is normally carried out at temperatures from $-10°$ to $40°$ C., in particular $-5°$ to $30°$ C., preferably $0°$ to $25°$ C.

The compounds of the general formula II can be prepared as given in EP-B 327,808, for example, for the hydrochloride.

The compounds of the general formula I can also be prepared, however, analogously to the process given in EP-B 327,808, by cyclisation of N-nitroso-N-(cis-2,6-dimethylpiperidino)aminoacetonitrile of the formula III

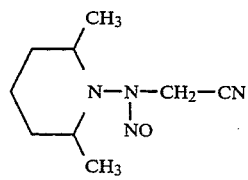 (III)

with phosphoric acid or with tartaric acid. The ratio compound of the formula III: acid is in this case preferably 1:1 to 1:10.

Suitable solvents for this reaction are, for example: alcohols, for example those having 1 to 8 C atoms, in particular those having 1 to 6 C atoms, preferably those having 1 to 4 C atoms, such as, for example, methanol, ethanol, i- and n-propanol, i-, sec- and tert-butanol, n-, i-, sec-, tert-pentanol, n-hexanol, 2-ethylbutanol, 2-ethylhexanol, isooctyl alcohol, cyclopentanol, cyclohexanol, methylcyclohexanol (mixture), benzyl alcohol; ethers, in particular those having 2 to 8 C atoms in the molecule, such as, for example, diethyl ether, methyl ethyl ether, di-n-propyl ether, di-isopropyl ether, methyl n-butyl ether, methyl tert-butyl ether, ethyl propyl ether, di-butyl ether, tetrahydrofuran, 1,4-dioxane, 1,2-dimethoxyethane, bis-β-methoxyethyl ether; oligoethylene glycol dimethyl ethers, such as, for example, tetraglyme or pentaglyme; alkyl carboxylates, in particular those having 2 to 10 C atoms in the molecule, such as, for example, methyl, ethyl, butyl or isobutyl formate, methyl, ethyl, propyl, isopropyl, butyl, isobutyl or sec-butyl, amyl, isoamyl, hexyl, cyclohexyl or benzyl acetate, methyl, ethyl or butyl propionate; ketones, in particular those having 3 to 10 C atoms in the molecule, such as, for example, acetone, methyl ethyl ketone, methyl n-propyl ketone, diethyl ketone, 2-hexanone, 3-hexanone, di-n-propyl ketone, di-isopropyl ketone, di-isobutyl ketone, cyclopentanone, cyclohexanone, methylcyclohexanone, dimethylcyclohexanone, benzophenone, acetophenone; aliphatic hydrocarbons, such as, for example, hexane, heptane, low- and high-boiling petroleum ethers, petroleum spirits and white spirit; cycloaliphatic hydrocarbons, such as, for example, cyclopentane, cyclohexane, methylcyclohexane, tetralin, decalin; aromatic hydrocarbons, such as, for example, benzene, toluene, o-, m- and p-xylene, ethylbenzene; halogenated aliphatic or aromatic hydrocarbons, such as, for example, methylene chloride, chloroform, carbon tetrachloride, 1,2-dichloroethane, chlorobenzene, dichlorobenzene, hexamethylphosphoramide; sulphoxides, such as, for example, dimethyl sulphoxide; tetramethylene sulphone; water. Mixtures of various solvents or dispersants can also be used, for example water-methanol or preferably ethyl acetate-methanol.

The cyclisation is normally carried out at temperatures from −10° to 40° C. in particular 0° to 40° C., preferably 0° to 20° C.

The compound of the formula III can be prepared as described in EP-B 327,808.

The pharmacological properties of the compounds of the general formula I are independent of the fact that they are dihydrogen phosphates or hydrogen tartrates. They lower the blood pressure as well as the pulmonary artery pressure and the left ventricular end-diastolic pressure and thus contribute to relief of the activity of the heart in the sense of an antianginal action, without at the same time provoking reflex tachycardia.

The compounds of the general formula I can therefore be administered to humans as medicines alone, in mixtures with one another or in the form of pharmaceutical preparations which enable enteral or parenteral administration and which as active constituent contain an effective dose of at least one compound of the general formula I in addition to customary pharmaceutically innocuous excipients and additives.

The medicines can be administered orally, for example in the form of pills, tablets, coated tablets, sugar-coated tablets, hard and soft gelatin capsules, solutions, syrups, emulsions or suspensions or aerosol mixtures. However, administration can also be carried out rectally, for example in the form of suppositories, or parenterally, for example in the form of injection solutions, or percutaneously, for example in the form of ointments or tinctures.

For the production of the pharmaceutical preparations, pharmaceutically inert inorganic or organic excipients can be used. For the production of pills, tablets, sugar-coated tablets and hard gelatin capsules, lactose, maize starch or derivatives thereof, talc, stearic acid or its salts, etc., for example, can be used. Excipients for soft gelatin capsules and suppositories are, for example, fats, waxes, semi-solid and liquid polyols, natural or hardened oils, etc. Suitable excipients for the production of solutions and syrups are, for example, water, sucrose, invert sugar, glucose, polyols, etc. Suitable excipients for the production of injection solutions are, for example, water, alcohols, glycerol, polyols or vegetable oils.

In addition to the active compounds and excipients, the pharmaceutical preparations can additionally contain additives, such as, for example, fillers, extenders, disintegrants, binders, lubricants, wetting agents, stabilisers, emulsifiers, preservatives, sweeteners, colorants, flavourings or aromatisers, buffer substances, and also solvents or solubilisers or agents for achieving a depot effect, as well as salts for altering the osmotic pressure, coating agents or antioxidants. They can also contain other therapeutically active substances.

Other therapeutically active substances of this type are, for example: β-receptor blockers, such as, for example, propranolol, pindolol, metoprolol; vasodilators, such as, for example, carbocromen; tranquillisers, such as, for example, barbituric acid derivatives, 1,4-benzodiazepines and meprobamate; diuretics, such as, for example, chlorothiazide; cardiotonic agents, such as, for example, digitalis preparations, hypotensive agents, such as, for example, hydralazine, dihydralazine, prazosin, clonidine, rauwolfia alkaloids; agents which decrease the fatty acid level in the blood, such as, for example, bezafibrate, fenofibrate; and agents for thrombosis prophylaxis, such as, for example, phenprocoumon.

The compounds of the general formula I and pharmaceutical preparations which contain the compounds of the general formula I as active compounds can be used in humans in the control or prevention of disorders of the cardiovascular system, for example as antihypertensive medicines in the various forms of high blood pressure, and in the control or prevention of angina pectoris, etc. The dose can vary within wide limits and is to be adapted to the individual conditions in each individual case. In general, in the case of oral administration a daily dose of about 0.5 to 100 mg, preferably 1 to 20 mg, per human individual is adequate. In the case of other administration forms, the daily dose, on account of the good absorption of the active compounds, is also in similar ranges of amounts, i.e. in general also 0.5 to 100 mg/human. The daily dose is normally divided into several part administrations, for example 2 to 4 part administrations.

EXAMPLES 1. 1. 3-(cis-2,6-Dimethylpiperidino)sydnone iminium hydrogen tartrate

A solution of 23.2 g of 3-(cis-2,6-dimethylpiperidino)-sydnone imine hydrochloride in 50 ml of water is cooled in an ice bath. After addition of 9.2 g of sodium bicarbonate, a solution of 16.5 g of L-(+)-tartaric acid in 15 ml of water is added dropwise and the mixture is additionally stirred in the ice bath. After 2 hours, the solid is filtered off with suction and recrystallised from a mixture of equal parts of water and methanol. The solid is washed with ethanol and then with ethyl acetate and dried.

Yield: 18.5 g

M.p. 170-2° C. (dec.)

$a_D^{20} = +12.46$ (c=H$_2$O/MeOH (1:1))

H$_2$O content (according to Fischer) <0.1%

2. The compound of Example 1 can also be obtained from 29.4 g of 3-(cis-2,6-dimethylpiperidino)sydnone iminium hydrogen sulphate and 18.5 g of sodium hydrogen carbonate as indicated there.

3. 3-(cis-2,6-Dimethylpiperidino)sydnone iminium dihydrogen phosphate

A mixture of 19.8 g of diammoniumhydrogen phosphate, 30 ml of water and 2.2 ml of 85% strength phosphoric acid is added dropwise to an ice-cooled solution of 29.4 g of 3-(cis-2,6-dimethylpiperidino)sydnone iminium hydrogen sulphate in 75 ml of water. After stirring for 1 hour, the solid is filtered off with suction.

Yield: 13.7 g

For further purification, the product can be recrystallised from water with the addition of 10% phosphoric acid or from water/ethanol or water/methanol mixtures.

M.p. 147° C. (dec.)

$H_2O$ content (according to Fisher) <0.1%

4. The compound of Example 3 can also be obtained by adding 89 g of orthophosphoric acid to a solution of 147 g of N-nitroso-N-(cis-2,6-dimethylpiperidino)aminoacetonitrile in 500 ml of ethyl acetate and allowing this mixture to stand for 3 days. The precipitate is then filtered off with suction and washed with ethyl acetate.

Yield: 96 g

M.p. 148° C. (dec.)

$H_2O$ content (according to Fisher): 0.05%

5. 3-(cis-2,6-Dimethylpiperidino)sydnone iminium hydrogen tartrate

A solution, cooled to 10° C., of 9.5 g of sodium hydroxide and 19.7 g of L-(+)-tartaric acid in 160 ml of water is added dropwise at 10° C. to a solution of 29.4 g of 3-(cis-2,6-dimethylpiperidino)sydnone iminium hydrogen sulphate in 100 ml of water. After stirring for one hour, the precipitated product is filtered off with suction, washed with 1% strength tartaric acid solution and dried.

Yield: 27.4 g.

6. The compound of Example 5 is obtained by dropwise addition of a solution of 8.0 g of sodium hydroxide and 16.5 g of L-(+)-tartaric acid in 100 ml of water to a solution of 29.4 g of 3-(cis-2,6-dimethylpiperidino)sydnone iminium hydrogen sulphate in 90 ml of water in a yield of 25.2 g as indicated there.

7. The compound of example 5 can also be obtained from 88.3 g of 3-(cis-2,6-dimethylpiperidino)sydnone iminium hydrogen sulphate in 325 ml of water and a solution of 70.9 g of ethanolamine and 108.6 g of L-(+)-tartaric acid in 220 ml of water as indicated there.

Yield: 93.2 g.

8. The compound of Example 5 is obtained by dropwise addition of a solution of 20.2 g of triethylamine and 16.5 g of tartaric acid in 30 ml of water to an ice-cooled solution of 29.4 g-of 3-(cis-2,6-dimethylpiperidino)sydnone iminium hydrogen sulphate in 100 ml of water in a yield of 29.3 g.

9. 3-(cis-2,6-Dimethylpiperidino)sydnone iminium dihydrogen phosphate

A solution of 15.1 g of diammonium hydrogen phosphate and 1.6 g of 85% strength phosphoric acid in 23 ml of water is added dropwise to a solution of 29.4 g of 3-(cis-2,6-dimethylpiperidino)sydnone iminium hydrogen sulphate in 75 ml of water. The reaction mixture is cooled, stirred in an ice bath for 2 hours, and the solid is filtered off with suction, washed with water and dried.

Yield: 14.7 g.

10. The compound of Example 9 is obtained by dropwise addition of a mixture of 30.3 g of triethylamine, 31.6 g of 85 per cent strength phosphoric acid and 30.0 ml of water to a solution of 29.4 g of 3-(cis-2,6-dimethylpiperidino)sydnone iminium hydrogen sulphate in 75 ml of water at 20 - 25° C in a yield of 20.6 g.

It is to be understood that the above described embodiments of the invention are illustrative only, and that modifications thereof may occur to those skilled in the art. Accordingly, this invention is not to be regarded as limited to the embodiments disclosed herein, but is to be limited only as defined by the appended claims.

We claim:

1. 3-(cis-2,6-Dimethylpiperidino)sydnone imine salt of the general formula I

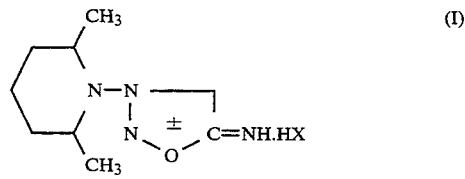

in which
X denotes $H_2PO_4$ or $$OOC-CH-CH-COOH.$$
$$\phantom{OOC-C}|\phantom{H-C}|$$
$$\phantom{OOC-CH-}OH\phantom{-C}OH$$

2. Compound of the formula

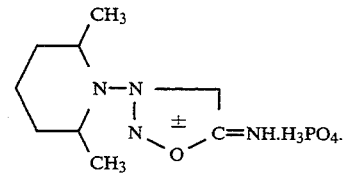

3. Compound of the formula

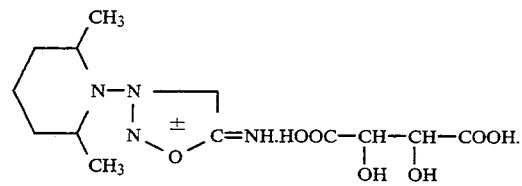

4. Pharmaceutical preparation, characterised in that it contains a compound according to claim 1 as active compound, together with pharmaceutically acceptable excipients and additives.

* * * * *